(12) United States Patent
Sasaki et al.

(10) Patent No.: US 8,916,178 B2
(45) Date of Patent: Dec. 23, 2014

(54) EMULSIFIED COSMETIC COMPOSITION

(75) Inventors: Kazutaka Sasaki, Yokohama (JP);
Takayuki Omura, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/143,425

(22) PCT Filed: Jan. 21, 2010

(86) PCT No.: PCT/JP2010/050682
§ 371 (c)(1),
(2), (4) Date: Sep. 16, 2011

(87) PCT Pub. No.: WO2010/084903
PCT Pub. Date: Jul. 29, 2010

(65) Prior Publication Data
US 2011/0318399 A1    Dec. 29, 2011

(30) Foreign Application Priority Data

Jan. 22, 2009   (JP) ................. 2009-011620

(51) Int. Cl.
*A61K 8/02* (2006.01)
*A61K 8/06* (2006.01)
*A61K 8/25* (2006.01)
*A61K 8/26* (2006.01)
*A61K 8/34* (2006.01)
*A61K 8/73* (2006.01)
*A61Q 19/00* (2006.01)

(52) U.S. Cl.
CPC ............. *A61K 8/06* (2013.01); *A61K 8/0254* (2013.01); *A61K 8/062* (2013.01); *A61K 8/25* (2013.01); *A61K 8/26* (2013.01); *A61K 8/345* (2013.01); *A61K 8/73* (2013.01); *A61Q 19/00* (2013.01)
USPC ........................................................ 424/401

(58) Field of Classification Search
None
See application file for complete search history.

(56) References Cited

U.S. PATENT DOCUMENTS

| 4,804,532 | A | * | 2/1989 | Busch, Jr. | 424/69 |
|---|---|---|---|---|---|
| 4,839,163 | A | * | 6/1989 | Busch, Jr. | 424/63 |
| 4,880,621 | A | * | 11/1989 | Grollier et al. | 424/74 |
| 5,171,572 | A | * | 12/1992 | Suganuma et al. | 424/401 |
| 5,540,921 | A | * | 7/1996 | Tanaka | 424/401 |
| 7,785,636 | B2 | * | 8/2010 | Fujiwara et al. | 424/709 |
| 2002/0081323 | A1 | | 6/2002 | Nakanishi et al. | |
| 2003/0086887 | A1 | * | 5/2003 | De La Poterie et al. | 424/70.11 |
| 2004/0266725 | A1 | * | 12/2004 | Inohara et al. | 514/54 |
| 2006/0013787 | A1 | * | 1/2006 | Sebillotte-Arnaud et al. | 424/70.11 |
| 2009/0060959 | A1 | * | 3/2009 | Igarashi | 424/401 |

FOREIGN PATENT DOCUMENTS

| JP | 07-017828 | 1/1995 |
|---|---|---|
| JP | 2001-199828 | 7/2001 |
| JP | 2001-342451 | 12/2001 |
| JP | 2004-175677 | 6/2004 |
| JP | 2006-131520 | 5/2006 |
| JP | 2007-210959 | 8/2007 |

OTHER PUBLICATIONS

Japanese Office Action Notice "Reasons for Rejection" for Pat. Appln. No. 2009-011620 dated Apr. 7, 2010, (JP and English and certificate of translation 5 pages).
Japanese Written Amendment for Pat. Appln. No. 2009-011620 dated Jun. 11, 2010, (JP and English and certificate of translation, 3 pages).
JapaneSe Written Argument for Pat. Appln. No. 2009-011620 dated Jun. 11, 2010 (JP and English and certificate of translation, 20 pages in total).
Decision to Grant a Patent for JP Pat. Appln. No. 2009-011620 dated Nov. 22, 2010 (JP and English and certificate of trananslation, 7 pages).
PCT/JP2010/050682—ISR (English and Japanese, 2 pages).
JP-A-2010-168302 Publication on Aug. 5, 2010 of Unexamined Patent Application JP No. 2009-011620 (JP and English and certificate of translation, 37 pages).
JP-B-4642905 JP Granted Patent, on Dec. 10, 2010, based on Patent Application JP No. 2009-011620 (JP and English and certificate of translation, 36 pages).
Keshouhin Seibun Yougo Jiten (Dictionary of Cosmetic Terms) 2008, Suzuki, Kazunari, 2008 Chuoshoin Publishing Co., Ltd., p. 71(2 pages), (English translation—1 page).
Pharmaceutical Bulletin, Entitled, "Protection of Organic Compounds by a Conceptional Diagram"; vol. 2, 2, pp. 163-173, Nov. 16, 1953, (11 pages).
Kagaku to Ryoiki, Journal of Japanese Chemistry, vol. 11, 10, pp. 719-725, published 1957.
Fragrance Journal, vol. 50, pp. 79-82, published 1981.
Shinban Yuuki Gainenzu-Kiso to Ouyou, New Edition, "The organic Conceptual Diagram, Its Fundamentals and Applications", Kouda Yoshio, et al., Sankyo Publishing Co., Ltd., 2008.
Korean Pat. Appln. No. 2011-7015659 Office Action dated Oct. 27, 2011, 4 pages—Korean, 5 pages—English.

* cited by examiner

*Primary Examiner* — Robert A Wax
*Assistant Examiner* — Olga V Tcherkasskaya
(74) *Attorney, Agent, or Firm* — Andrew F. Young, Esq.; Lackenbach Siegel, LLP

(57) ABSTRACT

Disclosed is an emulsified cosmetic which is not sticky, has a long-lasting moisturizing effect, and can realize an excellent shiny sensation after application. Specifically disclosed is an emulsified cosmetic characterized by comprising (A) 0.1 to 15% by mass of a plate-like powder, (B) 0.1 to 30% by mass of an oil having an IOB value of 0.1 to 0.5, (C) 0.01 to 5% by mass of a pulverized agar gel, and (D) 1 to 20% by mass of a moisturizing agent. The plate-like powder preferably has an average particle diameter of 1 to 20 μm. The pulverized agar gel is one obtained by dissolving agar in water or an aqueous solvent, then allowing the agar solution to cool and solidify to form a gel, and pulverizing the gel.

8 Claims, No Drawings

EMULSIFIED COSMETIC COMPOSITION

CROSS REFERENCE TO RELATED APPLICATIONS

This application relates to and claims priority from PCT/JP2010/050682 filed Jan. 21, 2010, the entire contents of which are incorporated herein by reference, which in turn claims priority from JP 2009-11620 filed Jan. 22, 2009 now issued as Japanese Pat. No. 4642905 on Dec. 10, 2010.

FIGURE SELECTED FOR PUBLICATION

No figures

BACKGROUND OF THE INVENTION

1. Field of the Invention

The present invention relates to skincare cosmetic compositions having a moisturizing effect. More specifically, the present invention relates to an emulsified cosmetic composition that contains an oil having a specific inorganic-organic-balance (IOB), a pulverized agar gel, a plate-like powder, and a moisturizing agent, so that it can have a long-lasting moisturizing effect without stickiness, and give an excellent shiny complexion.

2. Description of the Related Art

The water content of the skin stratum corneum is closely related to the maintenance of skin health and to the defense function against various external stimuli and plays an important role in preventing skin from aging and in maintaining moisture and smoothness ("Keshouhin Seibun Yougo Jiten (Dictionary of Cosmetic Ingredient Terms) 2008", SUZUKI, Kazunari, 2008, CHUOSHOIN Publishing Co., Ltd., page 71). The water content of the corneum is usually controlled by natural moisturizing factors (NMFs) and lipid membranes. However, their function is easily reduced by aging or external stimuli, and therefore it is important to supplement moisturizing components with moisturizing cosmetics so that the water content of the skin can be kept normal.

Many of moisturizing cosmetics conventionally used contain a water-soluble polyhydric alcohol such as propylene glycol, 1,3-butylene glycol or glycerin as a moisturizing agent. Unfortunately, such moisturizing cosmetics containing a water-soluble polyhydric alcohol have a sticky and a thick feel, although they exhibit a moisturizing effect, and moisturizing cosmetics containing such a general-purpose, water-soluble, polyhydric alcohol have the disadvantage that the persistence of the moisturizing effect is weak (see Patent Document 1, paragraph 0002).

JP-A 2006-131520 discloses that when a polyether adduct of a polyglycerin having a specific structure is added as a moisturizing agent alone or in combination with a conventional moisturizing agent, a moisturizing effect can last without stickiness.

JP-A 2007-210959 discloses a skin external preparation that has, by using a quince seed extract as a thickener, non-sticky and a light feel even when it has a high content of a moisturizing agent so as to increase moisturizing effect.

JP-A 2004-175677 discloses an aqueous gelatinous composition that contains a dispersion of spherical silicone particles in addition to a moisturizing agent and a water-soluble polymer (thickener), so that it has a dewy, light feel and good spreadability.

As described above, various attempts have been made to suppress the stickiness caused by moisturizing agents such as polyhydric alcohols and to improve the feeling of use, and some of them are successful to a certain extent. However, there is still a problem in which the resulting shiny sensation is weak particularly when conventional oil-in-water emulsions containing a moisturizing agent are applied, and there is no conventional technique capable of solving this problem.

ASPECTS AND SUMMARY OF THE INVENTION

Problems to be Solved by the Invention

Thus, an object of the present invention is to provide an emulsified cosmetic composition that is free of stickiness and not only has a long-lasting moisturizing effect but also gives an excellent shiny complexion after the application.

Means for Solving the Problems

As a result of keenly repeated studies to solve the problems, the inventors have accomplished the present invention based on the finding that when a plate-like powder, a specific oil having an IOB of 0.1 to 0.5 and a pulverized agar gel are used in combination with a moisturizing agent, a long-lasting moisturizing effect (moist feeling) and improved shiny complexion can be obtained without stickiness.

Specifically, the present invention provides an emulsified cosmetic composition including:
 (A) 0.1 to 15% by mass of a plate-like powder;
 (B) 0.1 to 30% by mass of an oil having an IOB of 0.1 to 0.5;
 (C) 0.01 to 5% by mass of a pulverized agar gel; and
 (D) 1 to 20% by mass of a moisturizing agent.

Effects of the Invention

The emulsified cosmetic composition of the present invention successfully maintains the moisturizing effect (moist feeling) of a moisturizing ingredient such as a polyhydric alcohol for a long time, is free of stickiness, and gives an excellent shiny complexion after application.

The above, and other aspects, features and advantages of the present invention will become apparent from the following description read in conjunction with the accompanying drawings, in which like reference numerals designate the same elements.

BRIEF DESCRIPTION OF THE DRAWINGS

None

DETAILED DESCRIPTION OF THE PREFERRED EMBODIMENTS

Modes for Carrying Out the Invention

In the emulsified cosmetic composition of the present invention, the plate-like powder (ingredient A) is not limited as long as it is the plate-like (flaky) powder generally used in cosmetics. Plate-like powders have been widely used in makeup cosmetics but are very rarely added to skin-care cosmetics such as those of the present invention. The plate-like powder has an aspect ratio (average particle diameter/average thickness) of more than 1, for example, at least 5 or more so that it can be distinguished from spherical powder. In the present invention, a plate-like powder with an average particle diameter of 1 to 20 min is preferably used, although the aspect ratio of the plate-like power is not specifically limited as long as it is plate-like (flaky).

Examples include plate-like powders made of mica, sericite, talc, kaolin, alumina, barium sulfate, boron nitride, N-acylated lysine, synthetic phlogopite, synthetic mica, synthetic talc, zinc oxide, silica, fish scale flake, bismuth oxychloride, and the like. These powders may be used singly or in combination of two or more. In the present invention, the plate-like powder may have undergone a surface treatment or no surface treatment.

In the present invention, the content of the plate-like powders (ingredient A) are from 0.1 to 15% by mass, preferably from 0.1 to 10% by mass, more preferably from 0.1 to 5% by mass. If the content is less than 0.1% by mass, the improvement of the shiny complexion may be insufficient, and if the powders are blended in an amount of more than 15% by mass, a rough feeling on the skin may be resulted.

In the emulsified cosmetic composition of the present invention, the oil having an IOB of 0.1 to 0.5 (ingredient B) is one having an IOB of 0.1 to 0.5 on the organic conceptual diagram. The organic conceptual diagram is a concept proposed by FUJITA Atsushi for indicating the polarity/nonpolarity of organic compounds, and the details thereof are described, for example, in "Pharmaceutical Bulletin", vol. 2, 2, pp. 163-173 (1954), "Kagaku no Ryoiki (Journal of Japanese Chemistry)" vol. 11, 10, pp. 719-725 (1957), and "Fragrance Journal", vol. 50, pp. 79-82 (1981). Briefly, the organic conceptual diagram is made by a process including assuming that methane ($CH_4$) is the source of all organic compounds and that the compounds other than methane are methane derivatives, selecting a certain numerical value for each of the number of carbon atoms, the substituent, the modified moiety, the ring, and the like, adding the scores to calculate the organic value (OV) and the inorganic value (IV), and plotting the organic value on the X axis and the inorganic value on the Y axis. IOB on the organic conceptual diagram refers to the ratio of the inorganic value (IV) to the organic value (OV), namely, "inorganic value (IV)/organic value (OV)" on the organic conceptual diagram. "Shinban Yuuki Gainenzu-Kiso to Ouyou- (New Edition, The Organic Conceptual Diagram, its Fundamentals and Applications)", (KOUDA Yoshio et al., SANKYO PUBLISHING Co., Ltd., 2008)" should be referred to for detailed description on the organic conceptual diagram.

In the present invention, if the oil to be added has an IOB of less than 0.1, a moisturizing effect cannot be obtained sufficiently, and if the oil has an IOB of more than 0.6, water-solubility is too high, and the oil may be dissolved and difficult to function as an oil.

Examples of the oil having an IOB of 0.1 to 0.5 that may be used in the present invention include, but are not limited to, ester oils such as octyl palmitate (IOB=0.13), cetyl 2-ethylhexanoate (IOB=0.13), cetyl octanoate (IOB=0.13), trimethylolpropane triisostearate (IOB=0.14), isopropyl myristate (IOB=0.18), glyceryl triisostearate (IOB=0.18), trimethylolpropane triisostearate (IOB=0.20), isononyl isononanate (IOB=0.20), isodecyl benzoate (IOB=0.23), isodecyl benzoate (IOB=0.23), neopentylglycol dicaprylate (IOB=0.25), neopentylglycol dicaprylate (IOB=0.25), diisostearyl malate (IOB=0.27), glyceryl diisostearate (IOB=0.29), trimethylolpropane triethylhexanoate (IOB=0.31), trimethylolpropane trioctanoate (IOB=0.31), propylene glycol dicaprylate (IOB=0.32), di-2-ethylhexyl succinate (IOB=0.32), pentaerythritol tetra(behenate/benzoate/ethylhexanoate) (IOB=0.35), trioctanoin (IOB=0.35), pentaerythrityl tetraethylhexanoate (IOB=0.35), pentaerythritol tetraoctanoate (IOB=0.35), pentaerythritol tetra-2-ethylhexanoate (IOB=0.35), glyceryl tri-2-ethylhexanoate (IOB=0.36), and diisopropyl sebacate (IOB=0.40); vegetable oils such as olive oil (IOB=0.16), castor oil (IOB=0.42), and macadamia nut oil (IOB=0.17); fatty acids such as isostearic acid (IOB=0.43) and oleic acid (IOB=0.42); higher alcohols such as decyl tetradecanol (IOB=0.21) and oleyl alcohol (IOB=0.28); and the like.

In the present invention, the content of the oil having an IOB of 0.1 to 0.5 (ingredient B) is from 0.1 to 30% by mass, preferably from 0.1 to 20% by mass, more preferably from 0.1 to 10% by mass. If the content is less than 0.1% by mass, the moisturizing effect may be insufficient, and a rough feeling on the skin may be caused by the powder formulation. If the content is more than 30% by mass, an unpleasant feeling of use such as a sticky feeling may occur.

In the emulsified cosmetic composition of the present invention, the pulverized agar gel (ingredient C) may be obtained by dissolving agar in water or an aqueous solvent, then allowing the agar solution to cool and solidify to form a gel, and pulverizing the gel. It is known that the pulverized agar gel produced as described above causes no sticky or squeaky feeling even when added to various preparations, and serves as a stable thickener for a long period without reducing viscosity even when other drug ingredients or salts are added in relatively large amounts thereto (see for example JP-A No. 2001-342451).

In the present invention, the content of the pulverized agar gel (ingredient C) is from 0.01 to 5% by mass, preferably from 0.01 to 3% by mass, more preferably from 0.01 to 1% by mass, on agar solid basis. If the content is less than 0.01% by mass, the effect of suppressing stickiness may be insufficient, and even if it is added in an amount of more than 5%, the effect cannot be further improved.

Further, besides the pulverized agar gel which has to have the above content, any thickener conventionally used in cosmetics, such as a carboxyvinyl polymer and a saccharide may be added to the emulsified cosmetic composition of the present invention so that the desired viscosity can be obtained, depending on the purpose or the intended use.

In the emulsified cosmetic composition of the present invention, the moisturizing agent (ingredient D) is not limited as long as it is a type conventionally used in cosmetics. Specific examples of the moisturizing agent include polyhydric alcohols such as glycerin (e.g., dynamite glycerol), propylene glycol, 1,3-butylene glycol, and sorbitol; mucopolysaccharides such as hyaluronic acid and chondroitin sulfate; natural moisturizing factors (NMFs) such as amino acids, pyrrolidone carboxylic acid (PCA), and lactic acid, or analogues thereof; intercellular lipids or analogues thereof; plant extracts; protein degradation products such as soluble collagen, elastin, and keratin; chitin; chitosan; yeast extracts; seaweed extracts; and the like.

In the present invention, the content of the moisturizing agent (ingredient D) is from 1 to 20% by mass, preferably from 5 to 20% by mass. If the content is less than 1% by mass, it will be difficult to obtain a moisturizing effect sufficiently, and addition of it in an amount of more than 20% by mass may cause a sticky feeling.

Besides the essential ingredients A to D described above, the emulsified cosmetic composition of the present invention may further contain other ingredients conventionally used in cosmetics, as long as the effects of the present invention are not interfered with. Examples of other ingredients include surfactants, alcohols, electrolytes, thickeners (other than the pulverized agar gel), preservatives, powders (other than the plate-like powder), pigments, dyes, ultraviolet absorbing agents, pH adjustors, perfumes, pharmaceutically effective ingredients, and the like.

Examples of surfactants include, but are not limited to, nonionic surfactants, anionic surfactants, cationic surfactants, ampholytic surfactants, and the like. Examples of nonionic surfactants include glycerin fatty acid esters and alkylene glycol adducts thereof, polyglyceryl fatty acid esters and alkylene glycol adducts thereof, propylene glycol fatty acid esters and alkylene glycol adducts thereof, sorbitan fatty acid esters and alkylene glycol adducts thereof, sorbitol fatty acid esters and alkylene glycol adducts thereof, polyalkylene glycol fatty acid esters, sucrose fatty acid esters, polyoxyalkylene alkyl ether, glycerin alkyl ether, polyoxyethylene alkyl phenyl ether, polyoxyethylene hydrogenated castor oil, alkylene glycol adducts of lanolin, polyoxyalkylene-modified silicone, polyether-modified silicone, and the like. Examples of anionic surfactants include inorganic and organic salts of fatty acids such as stearic acid and lauric acid, alkyl benzene sulfate, alkyl sulfonate, α-olefin sulfonate, diallyl, sulfosuccinate, α-sulfonated fatty acid salts, acylmethyl taurine salts, N-methyl-N-alkyl taurine salts, polyoxyethylene alkyl ether sulfate, polyoxyethylene alkyl phenyl ether sulfate, alkyl phosphate, polyoxyethylene alkyl ether phosphate, polyoxyethylene alkyl phenyl ether phosphate, N-acylamino acid salts, N-acyl-N-alkylamino acid salts, O-alkyl-substituted malate, alkyl sulfosuccinate, and the like. Examples of cationic surfactants include, for example, alkylamine salts, polyamine and alkanolamine fatty acid derivatives, alkyl quaternary ammonium salts, cyclic quaternary ammonium salts, and the like. Examples of ampholytic surfactants include amino acid sulfate, amino acid sulfonate, amino acid phosphate, phospholipids, and the like.

The emulsified cosmetic composition of the present invention may be produced by methods conventionally used for producing emulsions. For example, the emulsified cosmetic composition of the present invention may be obtained by mixing oil-phase ingredients containing the oil having an IOB of 0.1 to 0.5 (ingredient B), mixing aqueous-phase ingredients containing the pulverized agar gel (ingredient C) and the moisturizing agent (ingredient D) with the plate-like powder (ingredient A), mixing the aqueous phase and the oil phase, and emulsifying the mixture with a homomixer or the like.

The emulsified cosmetic composition of the present invention may be provided in the form of either an oil-in-water emulsion or a water-in-oil emulsion.

The present inventors consider that while a combination of the plate-like powder and the pulverized agar gel suppresses stickiness and provides a long-lasting moisturizing effect, the moisturizing effect of the oil having an IOB of 0.1 to 0.5 cancels out a rough feeling on the skin which could otherwise be manifested by the addition of the plate-like powder, so that the presence of the plate-like powder makes it possible to provide a better shiny complexion. While such a mechanism is not intended to limit the scope of the present invention, the effects of the present invention are obtained only by the specific combination of the ingredients A to D, and there is no prior art suggesting such a combination.

EXAMPLES

Hereinafter, the present invention is described in more detail and specifically with reference to some examples, which however are not intended to limit the scope of the present invention. Unless otherwise stated, the content is expressed in % by mass in the examples below and so on.

Test Examples 1 to 4

Emulsified cosmetic compositions were prepared, which were composed as shown in Table 1 below. An expert panel (three members) used the prepared emulsified cosmetic compositions of Test Examples 1 to 4 and evaluated them for "moist feeling," "stickiness" and "shiny complexion" immediately after and three hours after the application according to the criteria shown below. The results are also shown in Table 1.

Evaluation Criteria
(1) Moist Feeling
A: Significantly moisturizing
B: Moderately moisturizing
C: Not moisturizing
(2) Stickiness
A: Not sticky at al
B: Not sticky
C: Slightly sticky
D: Sticky
(3) Shiny complexion (visual judgment)
A: Good shiny complexion is observed.
B: Shiny complexion is observed.
C: No shiny complexion is observed.

In the visual judgment, the presence or absence of shiny complexion is visually judged.

TABLE 1

|  | Test Example 1 | Test Example 2 | Test Example 3 | Test Example 4 |
| --- | --- | --- | --- | --- |
| Water | 75.81 | 55.81 | 65.81 | 73.81 |
| Alcohol | 5 | 5 | 5 | 5 |
| Dynamiteglycerol | 5.6 | 5.6 | 5.6 | 5.6 |
| 1,3-butylene glycol | 5 | 5 | 5 | 5 |
| Caustic potash | 0.14 | 0.14 | 0.14 | 0.14 |
| Carboxyvinyl polymer | 0.25 | 0.25 | 0.25 | 0.25 |
| Alkyl (C12-18) acrylate copolymer | 0.05 | 0.05 | 0.05 | 0.05 |
| Xanthan gum | 0.1 | 0.1 | 0.1 | 0.1 |
| Agar | 0.36 | 0.36 | 0.36 | 0.36 |
| Succinoglycan | 0.09 | 0.09 | 0.09 | 0.09 |
| PEG-10 dimethicone | 0.1 | 0.1 | 0.1 | 0.1 |
| Mineral oil (IOB = 0) | 2 | 2 | 2 | 2 |
| Dimethicone (IOB = 0) | 5 | 5 | 5 | 5 |
| Pentaerythritol tetra-2-ethylhexanoate (IOB = 0.35) | — | 14 | 7 | 1.5 |
| Glyceryl diisostearate (IOB = 0.29) | — | 6 | 3 | 0.5 |
| Phenoxyethanol | 0.5 | 0.5 | 0.5 | 0.5 |
| Total | 100 | 100 | 100 | 100 |
| Immediately after |  |  |  |  |
| Moist feeling | B | A | A | A |
| Stickiness | B | D | D | C |
| Shiny complexion (visual judgment) | B | C | C | C |
| 3 hours after |  |  |  |  |
| Moist feeling | C | A | A | A |
| Stickiness | B | C | C | B |
| Shiny complexion (visual judgment) | B | C | C | C |

As is evident from the results shown in Table 1, in the plate-like-powder-free emulsified cosmetic compositions (Test Examples 1 to 4), those containing an oil having an IOB of 0.1 to 0.5 (Test Examples 2 to 4), gave improved "moist feeling", namely, improved moisturizing effects, as compared with the cosmetic composition not containing such an oil (Test Example 1). The improvement effect was particularly significant 3 hours after the application. However, the resulting "shiny complexion" was not improved.

Examples 1 to 3 and Comparative Examples 1 to 3

Emulsified cosmetic compositions were prepared, which were composed as shown in Table 2 below. An expert panel (three members) used the prepared emulsified cosmetic compositions of Examples 1 to 3 and Comparative Examples 1 to 3 and evaluated them for "moist feeling," "stickiness" and "shiny complexion" immediately after and three hours after the application according to the criteria described above for the test examples. The results are also shown in Table 2.

TABLE 2

|  | Comparative Example 1 | Comparative Example 2 | Example 1 | Example 2 | Example 3 | Comparative Example 3 |
|---|---|---|---|---|---|---|
| Water | 72.81 | 72.81 | 72.81 | 68.81 | 68.81 | 73.17 |
| Alcohol | 5 | 5 | 5 | 5 | 5 | 5 |
| Dynamiteglycerol | 5.6 | 5.6 | 5.6 | 5.6 | 5.6 | 5.6 |
| 1,3-butylene glycol | 5 | 5 | 5 | 5 | 5 | 5 |
| Caustic potash | 0.14 | 0.14 | 0.14 | 0.14 | 0.14 | 0.14 |
| Carboxyvinyl polymer | 0.25 | 0.25 | 0.25 | 0.25 | 0.25 | 0.25 |
| Alkyl (C12-18) acrylate copolymer | 0.05 | 0.05 | 0.05 | 0.05 | 0.05 | 0.05 |
| Xanthan gum | 0.1 | 0.1 | 0.1 | 0.1 | 0.1 | 0.1 |
| Agar | 0.36 | 0.36 | 0.36 | 0.36 | 0.36 | — |
| Succinoglycan | 0.09 | 0.09 | 0.09 | 0.09 | 0.09 | 0.09 |
| PEG-10 dimethicone | 0.1 | 0.1 | 0.1 | 0.1 | 0.1 | 0.1 |
| Mineral oil (IOB = 0) | 2 | 2 | 2 | 2 | 2 | 2 |
| Dimethicone (IOB = 0) | 5 | 5 | 5 | 5 | 5 | 5 |
| Pentaerythritol tetra-2-ethylhexanoate (IOB = 0.35) | 1.5 | 1.5 | 1.5 | 1.5 | 1.5 | 1.5 |
| Glyceryl diisostearate (IOB = 0.29) | 0.5 | 0.5 | 0.5 | 0.5 | 0.5 | 0.5 |
| Starch | 1 | — | — | — | — | — |
| Titanium oxide (pigment) | — | 1 | — | — | — | — |
| Synthetic phlogopite (plate-like powder) | — | — | 1 | 5 | — | 1 |
| Talc (plate-like powder) | — | — | — | — | 5 | — |
| Phenoxyethanol | 0.5 | 0.5 | 0.5 | 0.5 | 0.5 | 0.5 |
| Total | 100 | 100 | 100 | 100 | 100 | 100 |
| Immediately after |  |  |  |  |  |  |
| Moist feeling | A | A | A | A | A | A |
| Stickiness | C | C | B | B | B | D |
| Shiny complexion (visual judgment) | C | C | B | B | B | B |
| 3 hours after |  |  |  |  |  |  |
| Moist feeling | A | A | A | A | A | A |
| Stickiness | B | B | B | B | B | C |
| Shiny complexion (visual judgment) | C | C | B | B | B | B |

The emulsified cosmetic compositions shown in Table 2 all contained an oil with an IOB of 0.1 to 0.5 and therefore gave an improved "moist feeling" as compared with the emulsified cosmetic composition of Test Example 1 above. However, Comparative Examples 1 and 2 containing starch or titanium oxide (pigment) rather than plate-like powder were sticky as compared with Test Example 1 and still gave low shiny complexion. In contrast, Examples 1 to 3 containing a plate-like powder (synthetic phlogopite or talc) was no longer sticky and gave significantly improved shiny complexion. However, Comparative Example 3 containing a plate-like power but not containing a pulverized agar gel was found to cause stickiness.

Preparation Example 1

Skin Cream

| Ingredients | Content (% by mass) |
|---|---|
| (1) PEG-10 dimethicone | 0.1 |
| (2) Pentaerythritol tetra-2-ethylhexanoate (IOB = 0.35) | 1.5 |
| (3) Mineral oil | 2 |
| (4) Dimethicone | 5 |
| (5) Glyceryl diisostearate (IOB = 0.29) | 0.5 |

-continued

| Ingredients | Content (% by mass) |
|---|---|
| (6) Agar | 0.36 |
| (7) Carboxyvinyl polymer | 0.25 |
| (8) Alkyl (12-18) acrylate copolymer | 0.05 |
| (9) Xanthan gum | 0.1 |
| (10) Succinoglycan | 0.09 |
| (11) Glycerin | 5 |
| (12) 1,3-butylene glycol | 5 |
| (13) Synthetic phlogopite | 1 |
| (14) Phenoxyethanol | 0.5 |
| (15) Caustic potash | 0.14 |

| Ingredients | Content (% by mass) |
|---|---|
| (16) Alcohol | 5 |
| (17) Water | balance |

Preparation Method:

The ingredients (1) to (5) were mixed and dissolved together at room temperature (oil phase). On the other hand, the ingredient (6) was dissolved in part of the water and solidified, and the solidified product was pulverized and then mixed and dissolved with the ingredients (7) to (17) at room temperature (aqueous phase). The oil phase was added to the resulting aqueous phase, and the mixture was emulsified with a homomixer to give the desired skin cream.

Preparation Example 2

Skin Emulsion

| Ingredients | Content (% by mass) |
|---|---|
| (1) PEG-10 dimethicone | 0.03 |
| (2) Diisostearyl malate (IOB = 0.27) | 2 |
| (3) Mineral oil | 2 |
| (4) Dimethicone | 3 |
| (5) Agar | 0.5 |
| (6) Carboxyvinyl polymer | 0.15 |
| (7) Alkyl (12-18) acrylate copolymer | 0.05 |
| (8) Hydroxyethyl cellulose | 0.1 |
| (9) Succinoglycan | 0.1 |
| (10) Glycerin | 4 |
| (11) 1,3-butylene glycol | 7 |
| (12) Talc | 1 |
| (13) Phenoxyethanol | 0.5 |
| (14) Caustic potash | 0.06 |
| (15) Alcohol | 5 |
| (16) Water | balance |

Preparation Method:

The ingredients (1) to (4) were mixed and dissolved together at room temperature (oil phase). On the other hand, the ingredient (5) was dissolved in part of the water and solidified, and the solidified product was pulverized and then mixed and dissolved with the ingredients (6) to (16) at room temperature (aqueous phase). The oil phase was added to the resulting aqueous phase, and the mixture was emulsified with a homomixer to give the desired skin emulsion.

INDUSTRIAL APPLICABILITY

The emulsified cosmetic composition of the present invention suppresses the stickiness which would otherwise be caused by a moisturizing agent, gives a refreshing feeling of use, and not only has a long-lasting moisturizing effect but also gives the significantly improved shiny complexion which has been difficult to obtain from the conventional emulsified cosmetic compositions. Therefore, the emulsified cosmetic composition of the present invention may be used as a skin-care composition having a moisturizing effect without being modified. Taking advantage of the characteristics described above, the emulsified cosmetic composition of the present invention may also be used as a base for skincare cosmetic preparations containing active ingredients such as vitamin C.

The invention claimed is:

1. An emulsified skin-care cosmetic composition comprising:
    (A) 0.1 to 10% by mass of a plate-like powder;
    (B) 0.1 to 30% by mass of an oil having an inorganic-organic balance (IOB) of 0.1 to 0.5;
    (C) 0.01 to 5% by mass of a pulverized agar gel; and
    (D) 1 to 20% by mass of a moisturizing agent;
    wherein the oil component is selected from the group consisting of octyl palmitate (IOB=0.13), cetyl 2-ethylhexanoate (IOB=0.13), cetyl octanoate (IOB=0.13), trimethylolpropane triisostearate (IOB=0.14), isopropyl myristate (IOB=0.18), glyceryl triisostearate (IOB=0.18), trimethylolpropane triisostearate (IOB=0.20), isononyl isononate (IOB=0.20), isodecyl benzoate (IOB=0.23), neopentylglycol dicaprylate (IOB=0.25), diisostearyl malate (IOB=0.27), glyceryl diisostearate (IOB=0.29), trimethylolpropane triethylhexanoate (IOB=0.31), trimethylolpropane trioctanoate (IOB=0.31), propylene glycol dicaprylate (IOB=0.32), di-2-ethylhexyl succinate (IOB=0.32), pentaerythritol tetra(behenate/benzoate/ethylhexanoate) (IOB=0.35), trioctanoin (IOB=0.35), pentaerythrityl tetraethylhexanoate (IOB=0.35), pentaerythritol tetraoctanoate (IOB=0.35), pentaerythritol tetra-2-ethylhexanoate (IOB=0.35), glyceryl tri-2-ethylhexanoate (IOB=0.36), diisopropyl sebacate (IOB=0.40), decyl tetradecanol (IOB=0.21) and oleyl alcohol (IOB=0.28), and wherein said composition exhibits reduced stickiness relative to emulsified skin-care cosmetic compositions containing a non-pulverized agar gel.

2. The emulsified skin-care cosmetic composition according to claim 1, wherein the plate-like powder has an average particle diameter of 1 to 20 μm.

3. The emulsified skin-care cosmetic composition according to claim 1, wherein the pulverized agar gel is obtained by dissolving agar in an aqueous solvent, then allowing the agar solution to form a gel, and pulverizing the gel.

4. The emulsified skin-care cosmetic composition according to claim 1, which is an oil-in-water emulsion.

5. The emulsified skin-care cosmetic composition according to claim 1, wherein:
    the plate-like powder is selected from the group consisting of plate-like powders made of mica, sericite, talc, kaolin, alumina, barium sulfate, boron nitride, N-acylated lysine, synthetic phlogopite, synthetic mica, synthetic talc, zinc oxide, silica, fish scale flake, and bismuth oxychloride.

6. The emulsified skin-care cosmetic composition according to claim 5, wherein the plate-like powder has an average particle diameter of 1 to 20 μm.

7. The emulsified skin-care cosmetic composition according to claim 5, wherein the pulverized agar gel is obtained by dissolving agar in an aqueous solvent, then allowing the agar solution to form a gel, and pulverizing the gel.

8. The emulsified skin-care cosmetic composition according to claim 5, which is an oil-in-water emulsion.

* * * * *